United States Patent
McShirley

[11] 3,979,830
[45] Sept. 14, 1976

[54] DENTAL AMALGAM CARRIER

[76] Inventor: Robert C. McShirley, 6535 San Fernando Road, Glendale, Calif. 91201

[22] Filed: Nov. 24, 1975

[21] Appl. No.: 634,831

[52] U.S. Cl. .................................................. 32/60
[51] Int. Cl.² ........................................ A61C 5/04
[58] Field of Search ................... 32/60, 69; 128/21

[56] References Cited
UNITED STATES PATENTS

| 163,578 | 5/1875 | Cogswell | 32/69 |
|---|---|---|---|
| 2,434,311 | 1/1948 | Dean | 32/60 |
| 2,574,217 | 11/1951 | Lundgren et al. | 32/69 |

*Primary Examiner*—G.E. McNeill
*Attorney, Agent, or Firm*—Blakely, Sokoloff, Taylor & Zafman

[57] ABSTRACT

A dental instrument for carrying amalgam from a mixing station to a patient's tooth cavity. The instrument includes an elongated handle which is rotatably coupled to a mirror frame. This frame supports an amalgam carrying bucket and a mirror. The bucket swings away from the frame for filling, and is locked in place, adjacent to the mirror for transferring amalgam into a cavity.

11 Claims, 10 Drawing Figures

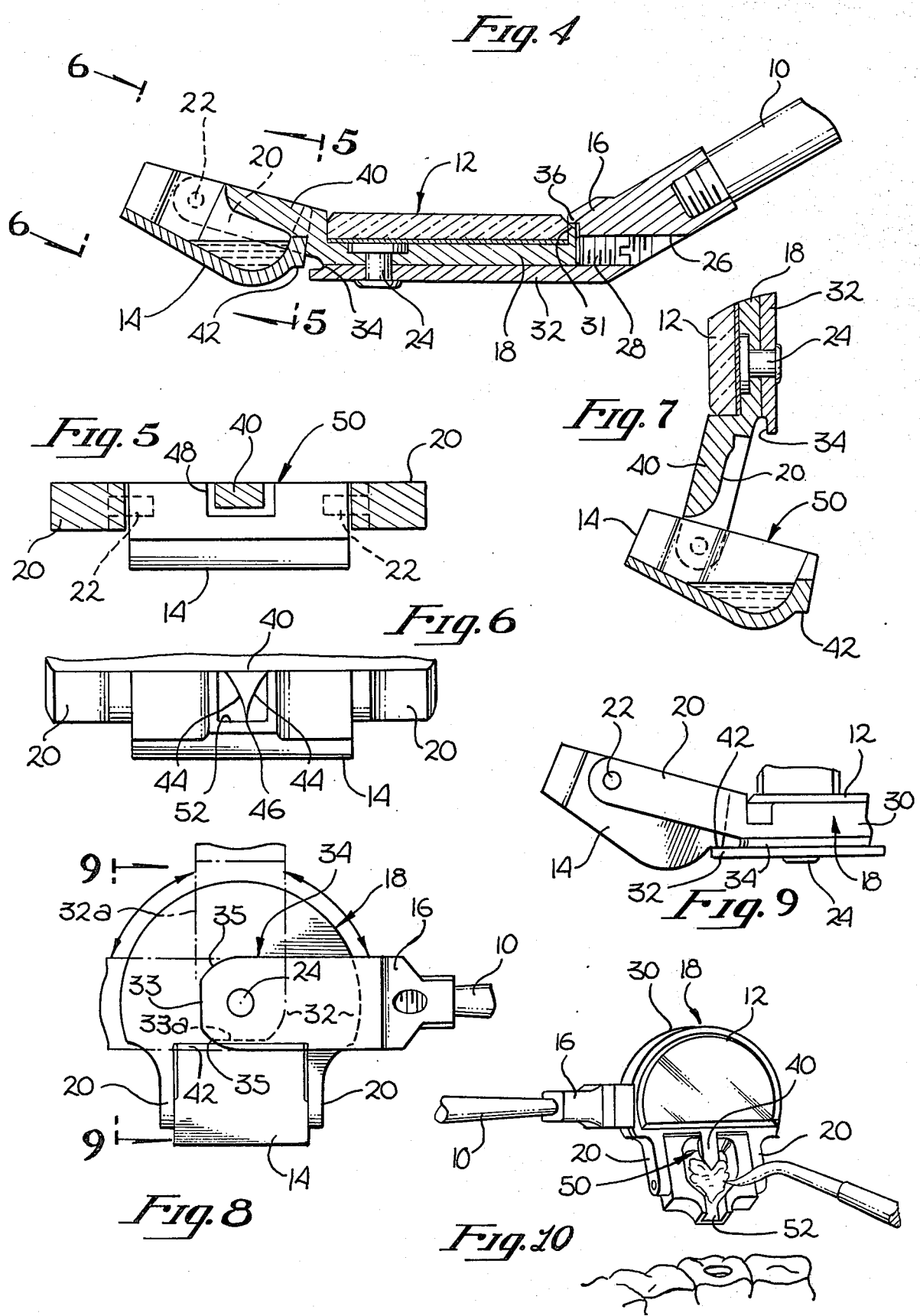

3,979,830

DENTAL AMALGAM CARRIER

BACKGROUND OF THE INVENTION

1. Field of the Invention

The invention relates to the field of dental amalgam carrying tools and instruments.

2. Prior Art

Dental amalgam is a predetermined ratio of silver alloy and mercury combined by a process of mixing in a mortar with pestle, or a mechanical amalgamator. After amalgamation it is a plastic mass which is carried to the tooth cavity and condensed as soon as possible because as soon as it is mixed, amalgam begins to set-up. A general rule is that it cannot be successfully condensed after three minutes.

The most commonly used instrument for transferring amalgam to a patient is a carrier which includes an elongated cylinder having a nozzle and a plunger. The nozzle is pressed into the freshly mixed amalgam to fill the space from the end of the nozzle to the face of the plunger. The nozzle is approximately 3/32 inch (inside diameter) and the depth to the plunger is typically approximately ¼ inch. The amalgam is then ejected into the cavity when the plunger is pushed forward. After each ejection the amalgam must be condensed for adaptation to the cavity. In some cases the amount of amalgam that is ejected is difficult to condense for complete adaptation to the cavity. Additional amalgam is added by reloading the carrier and this process continues until the cavity is complete filled. A mirror is generally used to deflect light or to view the cavity. To complete an amalgam restoration the dentist must interchange instruments which obviously slows the filling process. Since time is of the essence inferior fillings may occur as it is understood that the amalgam is setting-up, and further the amalgam may not be well condensed due to the amount ejected as previously stated.

As will be seen the invented amalgam carrier carries the total mix at one loading and is designed to hold the amalgam in a position from which the dentist rapidly transfers the amalgam directly into the cavity, little-by-little. The carrier permits good adaptation in a very short time and in most cases the amalgam restoration is completed with a single loading. The mirror in the carrier reflects light into the working area and also provides a means for viewing the progress of the filling procedure.

SUMMARY OF THE INVENTION

A dental tool or instrument is described for carrying amalgam, or the like, from a mixing station to a cavity. The tool includes a frame member which is pivotally coupled to an elongated handle through a support member. The frame member in addition to defining a frame for a mirror also includes a pair of spaced-apart support arms. An amalgam carrying bucket is rotatably coupled between these support arms such that the bucket may be rotated or swung away from the mirror for filling. Once amalgam is placed within the bucket and the bucket is brought into register with the frame and mirror, the frame is pivoted or swiveled on the support member locking the bucket in place. In this manner, when the bucket is held adjacent to a cavity, the amalgam may be urged from the bucket while the cavity is viewed in the mirror.

BRIEF DESCRIPTION OF THE DRAWINGS:

FIG. 4 is a partial cross-sectional view of the carrier taken along section line 4—4 of FIG. 3;

FIG. 5 is a cross-sectional view illustrating primarily the bucket and support arms taken along section line 5—5 of FIG. 4;

FIG. 6 is an end view of the bucket and support arms taken along section line 6—6 of FIG. 4;

FIG. 7 is a partial cross-sectional view of the carrier illustrating the bucket in its filling position;

FIG. 8 is a partial plan view of the underside of the carrier. This view is used to illustrate the manner in which the support member locks the bucket in place when it is swiveled;

FIG. 9 is a partial elevation view taken along section line 9—9 of FIG. 8; and

FIG. 10 is a perspective view illustrating amalgam being urged from the bucket into a cavity.

DETAILED DESCRIPTION OF THE INVENTION:

A dental tool and instrument for carrying amalgam from a mixing station to a cavity in a patient's tooth is described. The disclosed instrument as will be seen may be readily fabricated from metal such as stainless steel, employing known technology.

Figure 1:
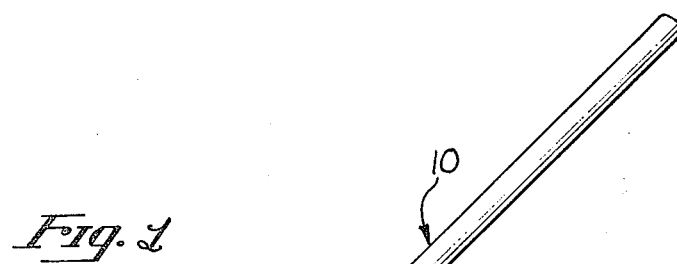
FIG. 1 is a perspective view illustrating the invented dental amalgam carrier.

Referring first to FIG. 1, the major components of the carrier include an elongated handle 10 which is threadedly coupled to a support member 16. A frame member 18 is pivotally coupled by a in 24 (FIG. 2) to the support arm 32 of support member 16. One surface of the frame includes a mirror 12 which is disposed adjacent to an amalgam carrying bucket 14. The bucket 14 defines a bucket interior 50 in which amalgam is placed for carrying the amalgam from the dental station to the patient's cavity. Thus, the major components of the tool include the handle 10, support member 16, frame member 18, mirror 12, and bucket 14.

The handle 10 comprises an elongated cylindrical member best viewed in FIG. 1. One end of the handle 10 is threaded and cooperatively engages a threaded bore in the support member 16, best illustrated in FIG. 4.

Figure 2:
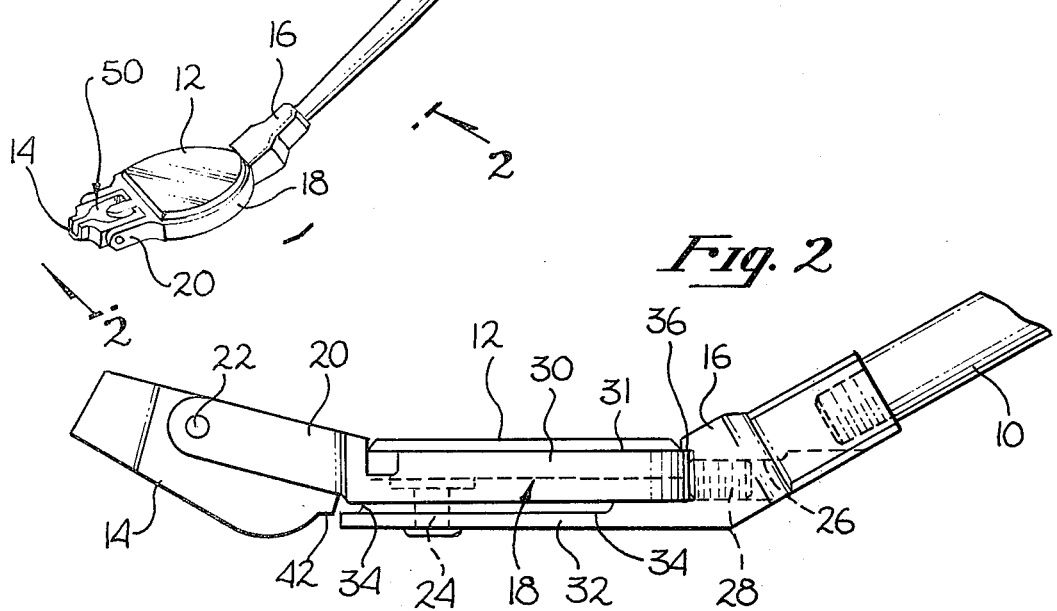
FIG. 2 is a partial elevation view of the carrier taken along section line 2—2 of FIG. 1.

The support member 16 includes a stock end which engages the handle 10 and a generally flat support arm 32. The upper surface of the support arm 32 provides a seat for the frame member 18. The frame member 18 is secured to the support member 16 by a pin 24 which is disposed adjacent to the distal end 33 of member 16 (FIG. 8). The end 33 of the support arm 32, as is best illustrated in FIG. 8, includes rounded corners 35 which interconnect the edges of the arm 32 with the distal end 32. The upper edges, corners 35 and distal end 33 of the arm 32 are undercut with undercut 34 illustrated in FIGS. 2, 4, 7 and 9. As will be explained this undercutting along with the shoulder 42 of bucket 14 (FIG. 4) provide a locking means to secure the bucket in place when the bucket is in register with the support arms 20, and when the frame member 18 is pivoted relative to the support member 16 on pin 24. The stock end of the support member 16 also defines a overlapping projection 36 which overlaps the mirror rim edge 31 as is shown in FIG. 2. An aperture 26 (FIGS. 2 and 4) is disposed through the stock end of the member 16. This aperture is threaded and receives a set screw 28 which projects through the aperture below the overlapping projection 36 to contact the mirror rim 30. This set screw provides a frictional surface to prevent the frame 18 from rotating too freely about the pin 24.

The frame member 18 illustrated in FIGS. 2, 3, 4, 7, 8, and 9 interconnects the support member 16 with the mirror 12 and the bucket 14. The frame member includes a generally semi-circular base which rests on the arm 32 and which is secured against this arm by the pin 24. Disposed about this semi-circular base is a mirror frame rim 30 which secures mirror 12 to the frame member 18. As mentioned, the edge 31 of this rim fits directly beneath the overlapping projection 36 and partly secures the frame to the support member 16. The ends of the frame member 18 define a pair of spaced-apart, parallel support arms 20, particularly well shown in FIGS. 2 and 3. An amalgam retaining finger 40 extends from a position on member 18 between the support arms 20, and is slightly skewed with these arms as will subsequently be explained. Referring briefly to FIG. 6, the amalgam engaging surfaces of the finger 40 include two concave surfaces 44 meeting at a common edge 46. These surfaces along with the edge 46 assist in compacting amalgam into the bucket after the bucket is filled.

The generally rectilinear bucket 14 includes a bucket cavity or interior 50 for receiving and transporting amalgam. The bucket 14 is mounted between the spaced-apart arms 20 and rotatably secured to these arms by a pair of pins 22, best illustrated in FIGS. 2, 3, 4, 7 and 9. The bucket 14 swings away from the arms 20 when being filled, as illustrated in FIG. 7, and when transporting amalgam is locked in place in register with the support arms 20, and adjacent to the mirror 12, as is illustrated in all of the Figures but FIG. 7. The front of the bucket 14 includes a outlet notch 52 which communicates with the interior of the bucket 50. Amalgam may be removed from the bucket through this outlet notch, as is best illustrated in FIG. 10. A notch 48 is disposed on the opposite side of the bucket from notch 52 (FIG. 5). Notch 48 allows the bucket to be moved into register with the support arms 20 without interference from the finger 40. When the bucket is in its closed position, the upper surfaces of the finger 40, bucket 14 and support arms 20 lie substantially in the same plane, which plane is at an obtuse angle with the mirror 12 as clearly seen in FIGS. 2 and 4.

The bottom, rearward portion of the bucket 14 defines a shoulder 42 which is clearly illustrated in FIGS. 2 and 4. The shoulder 42 extends from one side of the bucket to the other, as is best illustrated in FIG. 8. As will be explained this shoulder operates in conjunction with the undercut 34 of the support arm 32 for locking the bucket in register with the support arms 20 when the frame member 18 is rotated.

Figure 3:
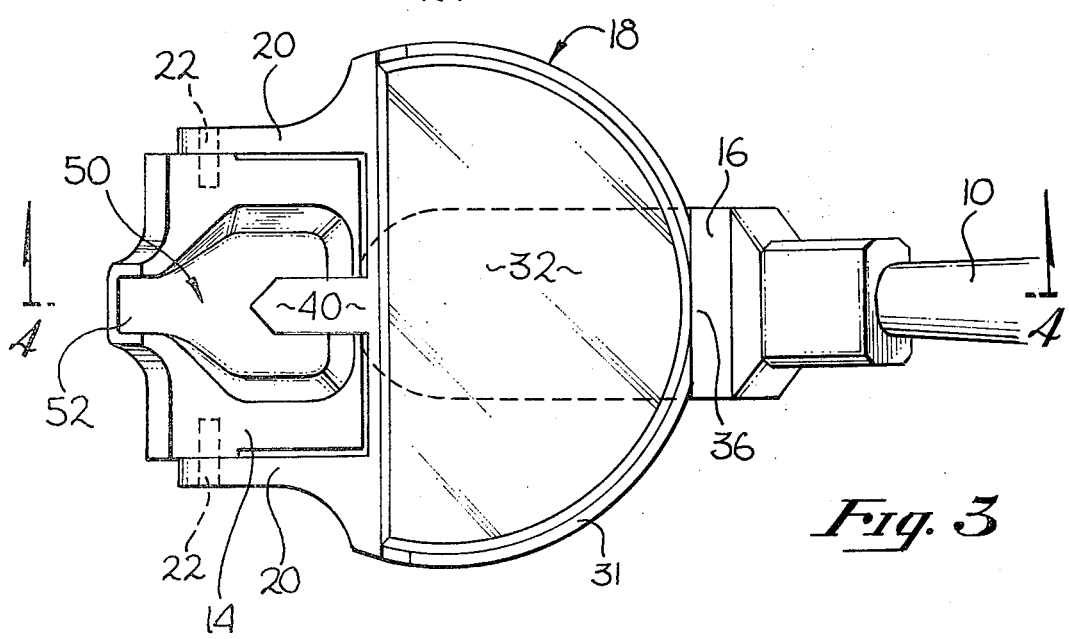
FIG. 3 is a partial plan view of the carrier illustrating the mirror and bucket.

Referring first to FIG. 3, the handle 10 is shown in-line with the finger 40 and outlet notch 42 (hereinafter referred to as the "in-line position"). This in-line position is also shown in FIGS. 2 and 4. Referring to FIG. 8 the in-line position is shown by support arm 32a, and as may be seen, the distal end 33a of the support arm 32a clears the shoulder 42 of bucket 14, thus allowing the bucket to rotate on the pins 22. Thus, when the frame member 18 is moved on pin 24 to this in-line position, the bucket 14 may be swung away for filling, as is illustrated in FIG. 7. Once the bucket is filled it then may be brought back to its closed position adjacent to the mirror 12.

when the frame 18 is pivoted on pin 24 away from the in-line position, the shoulder 42 extends within the undercut 34 thereby locking the bucket in place. This engagement is shown in FIGS. 8 and 9 where one edge of the support arm 32 is in interference with the shoulder 42. It will be appreciated that while in FIG. 8, the handle 10 is shown in a position approximately 90° from the in-line position, nonetheless the bucket is locked when the handle and frame are pivoted a few degrees from their in-line position since the corners 35 interfere with the shoulder 42.

To use the carrier, the handle 16 and support member 16 are rotated relative to the frame member 18 and bucket 14 to bring the handle and support member to the in-line position. In this position, the bucket 14 is then swung away from the arms, as shown in FIG. 7. In the presently preferred embodiment the finger 40 contacts one edge of the outlet notch 52, thereby limiting the swing of the bucket 14 to approximately the position shown in FIG. 7. Thus, the finger 40 is bent slightly towards one of the arms 20 to provide this interference. Once the bucket is in the position shown in FIG. 7 it may be readily filled with amalgam from the mixing station.

After the bucket is filled it is then swung to its closed position, such as is shown in FIGS. 2 and 4. The finger 40, and in particular the edge 46 and concave surfaces 44 (FIG. 6) compacts and retains amalgam within the bucket interior. Once the bucket is in register with the arms 20, the handle 10 and support member 16 may be pivoted relative to the frame member 18 and bucket 14 about the pin 24, thereby locking the bucket in place. Once this is accomplished the amalgam in the bucket may be transported to the patient's mouth and held adjacent to a cavity, such as is illustrated in FIG. 10. In this position amalgam may be urged with an ordinary dental tool from the interior of the bucket into the cavity, as is illustrated in FIG. 10. Since the mirror 12 is adjacent to the bucket 15, and hence adjacent to the patient's cavity, it allows the dentist to view the filling operation from a rearward perspective. Also, the handle 10 and frame member 16 may be moved into a plurality of different positions on either side of the bucket. This permits the filling of both lower and upper teeth, on either side of a patient's mouth.

Thus, a dental instrument has been disclosed which readily allows amalgam to be moved from a mixing station to a patient's tooth. Sufficient amounts of amalgam may be transported at one time to fill most cavities. The carrier includes a mirror which provides viewing for the dentist and for reflecting light into the cavity.

I claim:

1. A dental instrument for carrying amalgam, or the like comprising:
   a handle;
   a frame member, rotatably coupled to said handle;
   a bucket means for carrying amalgam, said bucket being coupled to said frame; and
   a mirror disposed on said frame member adjacent to said bucket;
   whereby said bucket may be filled with amalgam, or the like, and then rotated into a convenient position for filling a patient's cavity.

2. The dental instrument defined by claim 1 wherein said bucket is hingingly mounted to said frame member such that said bucket swings away from said frame member, particularly for filling.

3. The dental instrument defined by claim 2 including locking means for locking said bucket in a position adjacent to said mirror.

4. The dental instrument defined by claim 3 wherein said locking means locks said bucket in said position adjacent to said mirror when said frame member is rotated relative to said handle.

5. A dental instrument for carrying amalgam, or the like comprising:
 a handle;
 a frame member, rotatably coupled to said handle;
 a bucket means for carrying amalgam, said bucket means being rotatably coupled to said frame member such that said bucket means swings away from said frame member for filling;
 locking means for locking said bucket means in said frame member;
 whereby said bucket may be filled and then locked in place, and then rotated by rotating said frame member into a plurality of positions relative to a patient's cavity for filling the cavity with amalgam, or the like.

6. The dental instrument defined by claim 5, wherein a mirror is disposed on said frame member adjacent to said bucket means.

7. A dental instrument for carrying amalgam, or the like comprising:
 a handle, said handle including a support member;
 a frame, said frame being pivotally coupled to said support member and defining a pair of support arms;
 a mirror disposed within said frame;
 a bucket for carrying amalgam, said bucket being pivotally coupled between said support arms, said bucket defining an amalgam carrying interior and a notch through which amalgam contained within said bucket interior may be urged from said bucket interior;
 said bucket being pivotal on said support arms from a first position adjacent to said mirror to a filling position apart from said mirror;
 said bucket and support member defining locking means for locking said bucket in said first position when said frame is rotated relative to said handle to a predetermined relationship.

8. The dental instrument defined by claim 7 wherein said locking means includes a shoulder on said bucket and an undercut on said support member.

9. The dental instrument defined by claim 7 including a finger for retaining amalgam in said bucket.

10. The dental instrument defined by claim 9 wherein said bucket includes a notch for removing amalgam, or the like, and where an edge of said notch interfers with said finger when said bucket is in said filling position so as to limit the rotation of said bucket.

11. The dental instrument defined by claim 7 wherein said mirror is at an obtuse angle with the upper surface of said bucket when said bucket is in said first position.

* * * * *

UNITED STATES PATENT OFFICE
CERTIFICATE OF CORRECTION

Patent No. 3,979,830      Dated September 14, 1976

Inventor(s) Robert C. McShirley

It is certified that error appears in the above-identified patent and that said Letters Patent are hereby corrected as shown below:

Column 2, line 36, "in" should read -- pin --.

Column 4, line 5, at the beginning of the sentence, the "w" should be capatilized (W).

Signed and Sealed this

Thirtieth Day of November 1976

[SEAL]

Attest:

RUTH C. MASON
*Attesting Officer*

C. MARSHALL DANN
*Commissioner of Patents and Trademarks*